US00PP34385P3

(12) United States Plant Patent
Schoone

(10) Patent No.: US PP34,385 P3
(45) Date of Patent: Jun. 28, 2022

(54) ***PHALAENOPSIS* PLANT NAMED 'MOONLIGHT SERENADE'**

(50) Latin Name: *Phalaenopsis hybrida*
Varietal Denomination: Moonlight Serenade

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 39 days.

(21) Appl. No.: 17/339,977

(22) Filed: Jun. 5, 2021

(65) Prior Publication Data

US 2021/0386000 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Moonlight Serenade', characterized by its upright plant habit; moderately vigorous growth habit; strong flowering stems; strong leaves; freely flowering habit with typically two inflorescences per plant, each inflorescence with numerous flowers; flowers with fused labella; white-colored flowers with a large white-colored labella with light purple-colored stripes and marbling; and good postproduction longevity.

2 Drawing Sheets

Figure 1:
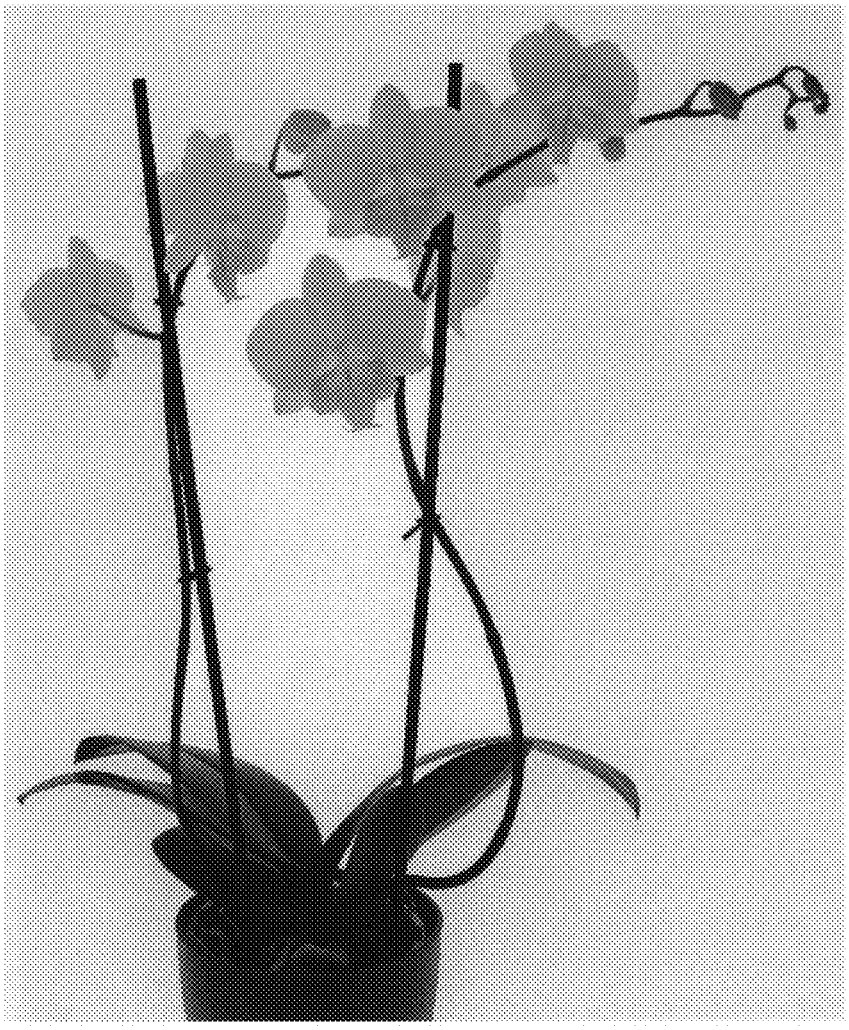

Botanical designation: *Phalaenopsis hybrida.*
Cultivar denomination: 'MOONLIGHT SERENADE'.

CROSS-REFERENCED TO CLOSELY-RELATED APPLICATIONS

Title: Varieties of *Phalaenopsis* Plants
Inventor: René Schoone
Filed: Jun. 6, 2020
Ser. No.: 62/705,003
Inventor and Applicant/Assignee hereby claims the benefit of this provisional U.S. Patent Application.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Mar. 18, 2021, application number 2021/0833. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Moonlight Serenade'.

The new *Phalaenopsis* plant is a product of a planned breeding program conducted by the Inventor in De Lier and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in July, 2012 in Nantou, Taiwan of *Phalaenopsis hybrida* 'Timothy Christopher', not patented, as the female, or seed, parent with *Phalaenopsis hybrida* 'Sogo Yukidian' X 'Yu Pin Firework', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in December, 2017.

Asexual reproduction of the new *Phalaenopsis* plant by in vitro meristem propagation in a controlled environment in Assendelft, The Netherlands since December, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Moonlight Serenade'. These characteristics in combination distinguish 'Moonlight Serenade' as a new and distinct *Phalaenopsis* plant:

1. Upright plant habit.
2. Moderately vigorous growth habit.
3. Strong flowering stems.
4. Strong leaves.
5. Freely flowering habit with typically two inflorescences per plant, each inflorescence with numerous flowers.
6. Flowers with fused labella, typically referred to as a "big lip" type.
7. White-colored flowers with a large white-colored labella with light purple-colored stripes and marbling.
8. Good postproduction longevity.

Plants of the new *Phalaenopsis* can be compared to plants of the female parent, 'Timothy Christopher'. Plants of the new *Phalaenopsis* differ primarily from plants of 'Timothy Christopher' in plant habit and flower size as plants of the new *Phalaenopsis* are taller and have broader flowers than plants of 'Timothy Christopher' are dark yellow in color with only a few spots and no dashes or stripes. In addition, the labellum lateral and central lobes are fused in plants of the new *Phalaenopsis* whereas the lateral and central lobes of the labellum of plants of 'Timothy Christopher' are not fused.

Plants of the new *Phalaenopsis* can be compared to plants of the male parent, 'Sogo Yukidan' X 'Yu Pin Firework'. Plants of the new *Phalaenopsis* differ primarily from plants of 'Sogo Yukidan' X 'Yu Pin Firework' in flower color as flower labella of plants of the new *Phalaenopsis* are white in color with light purple-colored stripes and marbling whereas flower labella of plants of 'Sogo Yukidan' X 'Yu Pin Firework' are solid white in color without any stripes or marbling.

Plants of the new *Phalaenopsis* can be compared to plants of *Phalaenopsis hybrida* 'Pillow Talk', not patented. In side-by-side comparisons, plants of the new *Phalaenopsis* differ primarily from plants of 'Pillow Talk' in flower color as flower labella of plants of the new *Phalaenopsis* are white in color with light purple-colored stripes and marbling whereas flower labella of plants of 'Pillow Talk' are white in color with only a few stripes and no marbling.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Moonlight Serenade' grown in a container.

Figure 2:
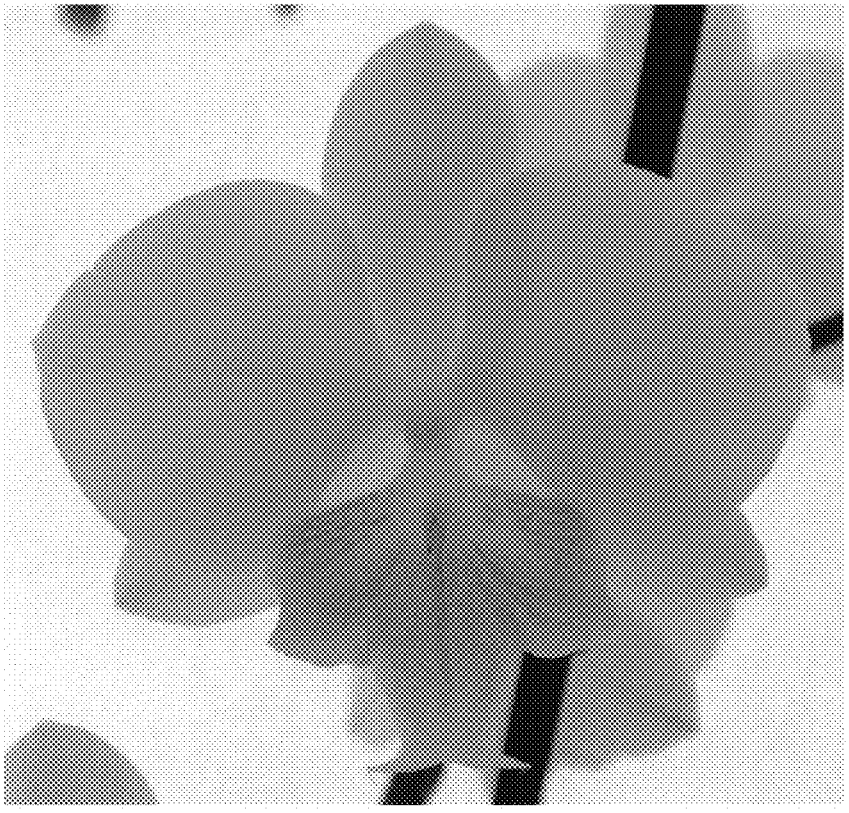

The photograph on the second sheet (FIG. 2) is a close-up view of a typical flower of 'Moonlight Serenade'.

DETAILED BOTANICAL DESCRIPTION

The aforementioned photographs and following observations and measurements describe plants grown during the spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Moonlight Serenade'.

Parentage:

*Female parent.*—*Phalaenopsis hybrida* 'Timothy Christopher', not patented.

*Male parent.*—*Phalaenopsis hybrida* 'Sogo Yukidan' X 'Yu Pin Firework', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; upright plant habit with typically two inflorescences per plant, each inflorescence with numerous flowers; monopodial; moderately vigorous growth habit and moderate growth rate.

*Plant height, substrate level to top of foliar plane.*—About 9.1 cm.

*Plant height, substrate level to top of inflorescences.*—About 40.8 cm.

*Plant diameter or spread.*—About 31.4 cm.

Leaf description:

*Arrangement and quantity.*—Distichous, simple; sessile; about six leaves per plant.

*Length.*—About 18.6 cm.

*Width.*—About 7.8 cm.

*Aspect.*—Upright to outwardly arching.

*Shape.*—Oblanceolate; slightly carinate.

*Apex.*—Unequal obtuse to unequal broadly acute.

*Base.*—Sheathing. Sheath length: About 1.4 cm. Sheath width: About 1.4 cm. Sheath color: Close to 143B; towards the upper margin, close to 146B.

*Margin*.—Entire.

*Texture and luster, upper and lower surfaces*.—Smooth, glabrous; slightly glossy.

*Venation pattern*.—Camptodromous.

*Color*.—Developing leaves, upper surface: Close to a blend of NN137A and 147A. Developing leaves, lower surface: Close to 146B heavily mottled with close to N186C. Fully expanded leaves, upper surface: Close to NN137B; margin edges, close to 144B; venation, close to NN137A. Fully expanded leaves, lower surface: Close to 146B slightly mottled with close to N186C; venation, close to 200C.

Inflorescence description:

*Appearance and flowering habit*.—Showy zygomorphic flowers arranged on axillary branched racemes; typically two inflorescences per plant; each inflorescence with about twelve flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 27 cm.

*Inflorescence width*.—About 11.6 cm.

*Flower buds*.—Height: About 2.3 cm. Diameter: About 1.3 cm by 1.5 cm. Shape: Ovate to broadly ovate. Color: Close to 145C slightly tinged with close to 174C.

*Flower size*.—About 7.5 cm (vertical) by 7.5 cm (horizontal).

*Flower depth*.—About 1.8 cm.

*Petals, quantity and arrangement*.—Three, two lateral petals and one center petal transformed into a labellum.

*Lateral petals*.—Length: About 3.7 cm. Width: About 3.9 cm. Shape: Reniform to short rhomboidal. Apex: Obtuse to very broadly and bluntly acute. Margin: Entire. Texture and luster, upper and lower surfaces: Smooth, glabrous, velvety; matte. Color: When opening, upper surface: Close to a blend of NN155A and NN155B. When opening, lower surface: Close to 157D; towards the margins and apex, close to NN155B. Fully opened, upper and lower surfaces: Close to NN155D; color does not change with subsequent development.

*Labella*.—Appearance: Lateral and central lobes fused towards the base into a single lobe, typically referred to as a "big lip" type. Length, lateral lobes: About 1.8 cm. Width, lateral lobes: About 1.9 cm. Length, central lobe: About 3.5 cm. Width, central lobe: About 9 mm. Shape, lateral and central lobes: Labellum overall, roughly reniform. Apex, lateral lobes: Obtuse. Apex, central lobe: Broadly retuse with two narrow forward-facing cirrose tips, about 7 mm in length and about 1.6 mm in width. Margins, lateral and central lobes: Entire. Texture and luster, upper and lower surfaces: Smooth, glabrous, moderately velvety; matte. Callosities: Located at the base of the labellum and attachment point of the lateral petals; about 4 mm in length, about 2 mm in width and about 3 mm in height. Color, lateral and central lobes: When opening, upper surface: Close to NN155B and towards the lateral lobe apices, close to NN155D with radial stripes and mottling, close to 75A to 75B; main vein on central lobe, close to N75A to N75B; at the base (at column connection), close to 157D. When opening, lower surface: Close to NN155B and towards the apex, close to 157C to 157D with faint radial stripes and mottling, close to 76B; at the base (at column connection), close to 157C to 157D. Fully opened, upper surface: Close to NN155D with radial stripes and mottling, close to 76A; main vein on central lobe, close to 70B; at the base (at column connection), close to 76A. Fully opened, lower surface: Close to NN155C with faint radial stripes and mottling, close to 76B. Color, callosities: Immature: Close to 150C to 150D with fine dots, close to N77B. Mature: Close to NN155A with fine dots, close to N77D.

*Sepals*.—Quantity and arrangement: Three, one upper dorsal sepal and two lower lateral sepals. Length, dorsal sepal: About 3.8 cm. Width, dorsal sepal: About 2.1 cm. Length, lateral sepals: About 3.8 cm. Width, lateral sepals: About 2 cm. Shape, dorsal sepal: Elliptic to oblong. Shape, lateral sepals: Ovate. Apex, dorsal sepal: Bluntly acute. Apex, lateral sepals: Acute. Base, dorsal and lateral sepals: Truncate. Margin, dorsal sepal: Entire. Margin, lateral sepals: Entire. Texture and luster, dorsal and lateral sepals, upper and lower surfaces: Smooth, glabrous, velvety; matte. Color, dorsal sepal: When opening, upper surface: Close to a blend of NN155A and NN155B. When opening, lower surface: Close to 150D; towards the margins and apex, close to 157C; slightly tinged with close to 181D. Fully opened, upper surface: Close to NN155D. Fully opened, lower surface: Close to NN155C; towards the apex, slightly tinged with close to 76C. Color, lateral sepals: When opening, upper surface: Distally, close to 155B and proximally, close to 150D with basal venation, close to 182D. When opening, lower surface: Close to 150D; towards the apex, tinged with close to 174D. Fully opened, upper surface: Close to NN155D; towards the apex, slightly tinged with close to 75C. Fully opened, lower surface: Close to NN155C; towards the apex, slightly tinged with close to 75C.

*Peduncles*.—Length: About 55.2 cm. Diameter: About 4.5 mm. Strength: Strong. Aspect: Upright to outwardly arching. Texture and luster: Smooth, glabrous; matte. Color: Close to 143A to 143B, densely covered with fine dots, close to 147A; towards the apex, darker than 197A.

*Pedicels*.—Length: About 3.8 cm. Diameter: About 2.75 mm. Strength: Moderately strong. Aspect: About 60° from peduncle axis. Texture and luster: Smooth, glabrous; matte. Color: Close to N148A; distally, close to 186D.

*Reproductive organs*.—Androecium: Column length: About 8 mm. Column width: About 5 mm. Column color: Close to NN155B. Pollinia quantity: Two. Pollinia diameter (per two pollinia): About 2 mm. Pollinia color: Close to 23A. Gynoecium: Stigma length: About 2.5 mm. Stigma width: About 4 mm. Stigma shape: Reniform. Stigma color: Close to NN155C. Ovary length: About 6 mm. Ovary diameter: About 1 mm. Ovary color: Close to 149D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Moonlight Serenade' as illustrated and described.

* * * * *